United States Patent [19]
Hillsman et al.

[11] Patent Number: 5,514,128
[45] Date of Patent: May 7, 1996

[54] FIBER OPTIC GUIDE WIRE AND SUPPORT CATHETER THEREFOR

[75] Inventors: Cecily M. Hillsman; Kevin D. Taylor, both of Colorado Springs, Colo.; Daniel J. Kasprzyk, Bethlehem, Pa.; Matthew S. Solar, Cooper City, Fla.

[73] Assignee: Spectranetics Corporation, Colorado Springs, Colo.

[21] Appl. No.: 225,061

[22] Filed: Apr. 8, 1994

Related U.S. Application Data

[63] Continuation-in-part of Ser. No. 930,934, Aug. 18, 1992, abandoned.

[51] Int. Cl.$^6$ .................................................. A61B 5/06
[52] U.S. Cl. .................... 606/7; 606/15; 128/772
[58] Field of Search .................. 606/2, 3, 7, 10–17; 607/89; 128/772

[56] References Cited

U.S. PATENT DOCUMENTS

| | | | |
|---|---|---|---|
| 4,456,017 | 6/1984 | Miles | 128/772 |
| 4,648,892 | 3/1987 | Kittrell . | |
| 4,662,368 | 5/1987 | Hussein . | |
| 4,672,961 | 6/1987 | Davies . | |
| 4,799,479 | 1/1989 | Spears | 606/7 |
| 4,819,632 | 4/1989 | Davies . | |
| 4,832,024 | 5/1989 | Boussignac . | |
| 4,834,093 | 5/1989 | Littleford . | |
| 4,844,062 | 7/1989 | Wells . | |
| 4,846,193 | 7/1989 | Tremulis et al. | 128/772 |
| 4,848,339 | 7/1989 | Rink . | |
| 4,850,351 | 7/1989 | Herman . | |
| 4,854,315 | 8/1989 | Stack . | |
| 4,920,967 | 5/1990 | Cottonaro . | |
| 4,929,246 | 5/1990 | Sinofsky . | |
| 4,932,413 | 6/1990 | Shockey . | |
| 4,940,062 | 7/1990 | Hampton . | |
| 4,947,864 | 8/1990 | Shockey . | |
| 4,958,642 | 9/1990 | Christian . | |
| 4,966,596 | 10/1990 | Kuntz . | |
| 4,967,745 | 11/1990 | Hayes et al. | 606/7 |
| 4,988,356 | 1/1991 | Crittenden . | |
| 5,009,655 | 4/1991 | Daignault, Jr. et al. | 606/7 |
| 5,030,217 | 7/1991 | Harrington . | |
| 5,035,686 | 7/1991 | Crittenden . | |
| 5,045,061 | 9/1991 | Seifert . | |
| 5,053,033 | 10/1991 | Clarke . | |
| 5,095,911 | 3/1992 | Pomeranz . | |
| 5,115,814 | 5/1992 | Griffith . | |
| 5,117,839 | 6/1992 | Dance . | |
| 5,188,634 | 2/1993 | Hussein et al. | 606/7 |
| 5,275,151 | 1/1994 | Shockey et al. | 128/772 |

FOREIGN PATENT DOCUMENTS

| | | |
|---|---|---|
| 0355996 | 2/1990 | European Pat. Off. . |
| 0163502 | 12/1995 | European Pat. Off. . |

*Primary Examiner*—Stephen C. Pellegrino
*Assistant Examiner*—Michael Peffley
*Attorney, Agent, or Firm*—Cushman, Darby & Cushman

[57] ABSTRACT

A guide wire for a catheter has a tubular portion with a flexible body fixed to its distal end. The distal end of the body may be composed of a radiopaque material. Optical fibers are disposed within the assembly and terminate in a radiopaque tip at the distal end of the body. The guide wire may have a longitudinal marker wire or mandrel for providing stiffness and radioscopic tracking characteristics, as well as providing torsional control and tip shaping capabilities. The guide wire has a proximal end attached to the tube and a distal end that also terminates in the tip. The wire may be maneuvered in a vascular area like a conventional guide wire and may be used in conjunction with a support catheter to increase its maneuverability. Then, laser energy is conveyed to the vascular area by the optical fibers to ablate an obstruction. The proximal end of the guide wire is then removed and a larger catheter may then be slid over the guide wire to continue the ablation operation. Employing plastic tubing, a wire coil, or a combination of these two for the distal body, the guide wire may be used in peripheral or coronary angioplasty applications. The guide wire may be used in conjunction with a support catheter which is used to direct the guide wire to a treatment site and provides improved tracking characteristics.

20 Claims, 9 Drawing Sheets

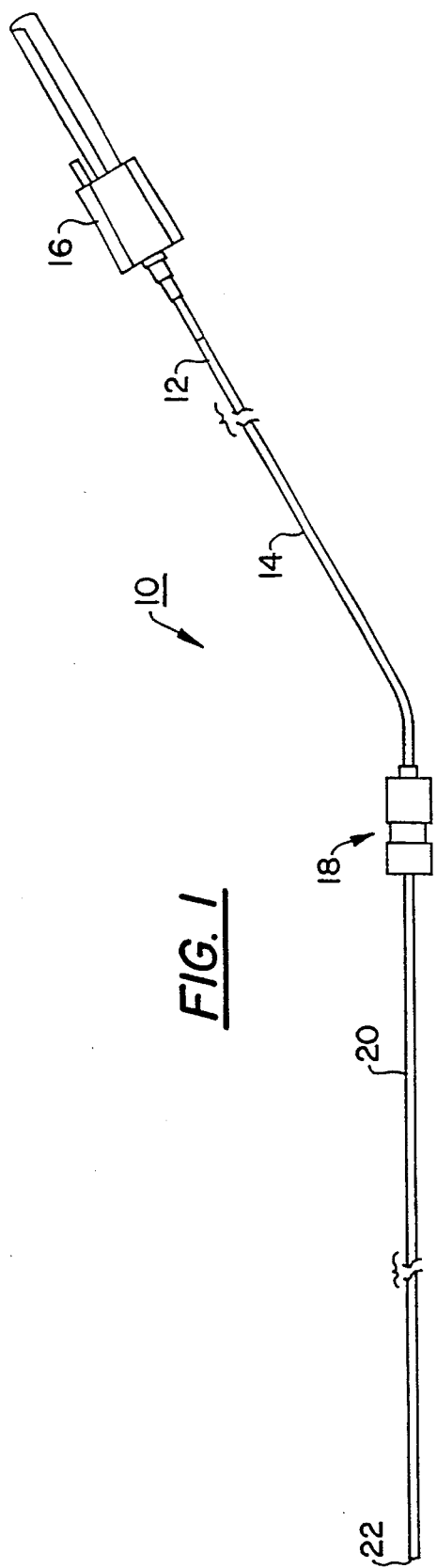
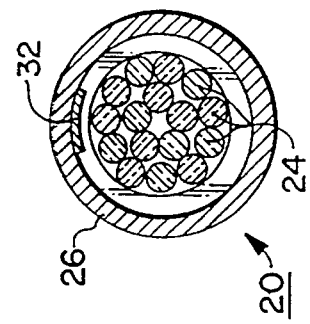
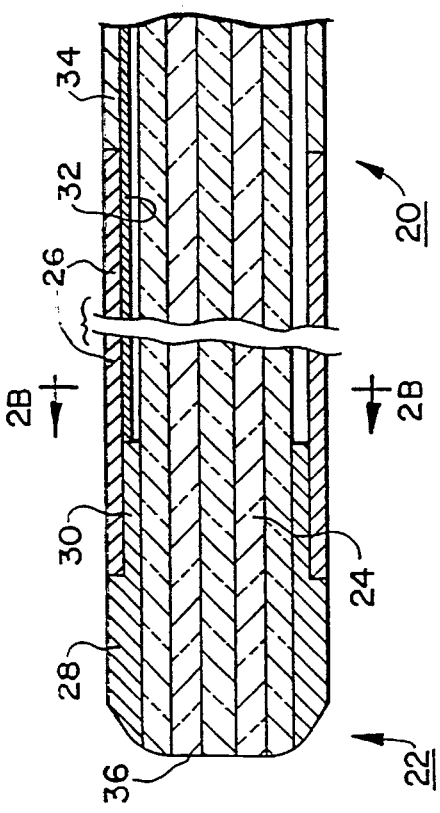
FIG. 1
FIG. 2B
FIG. 2A

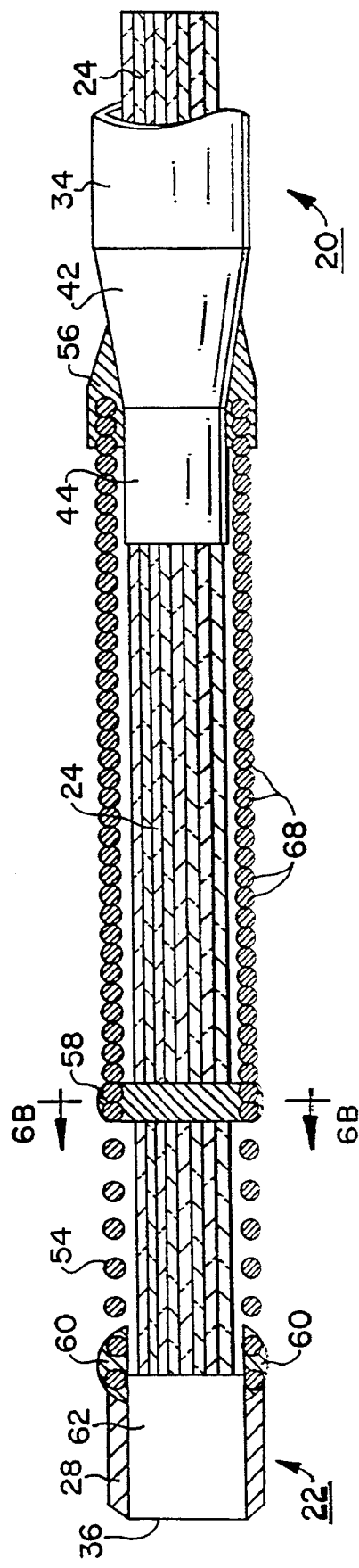
*FIG. 6A*
*FIG. 6B*
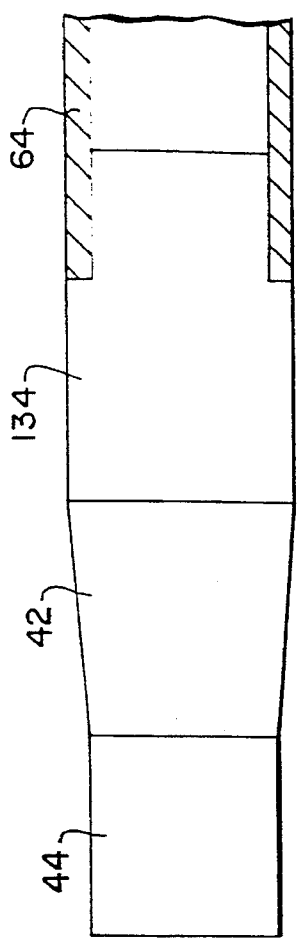
*FIG. 7*

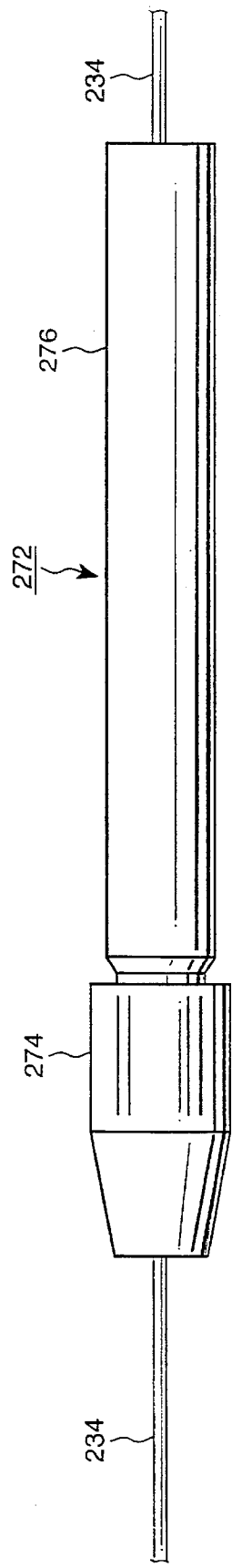
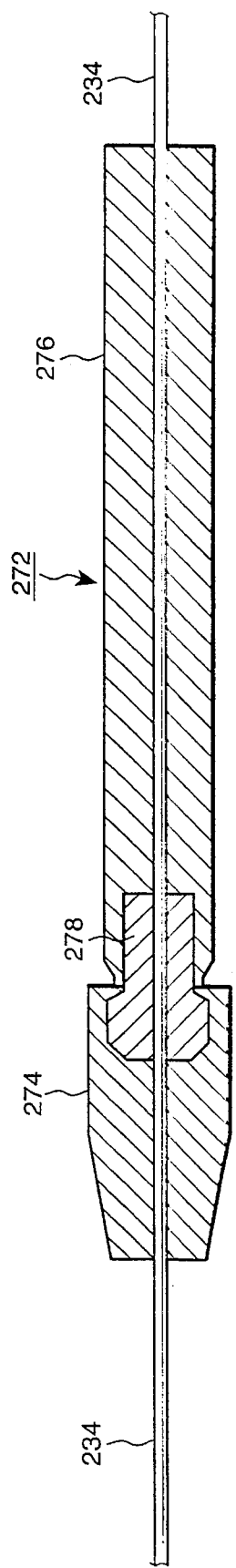

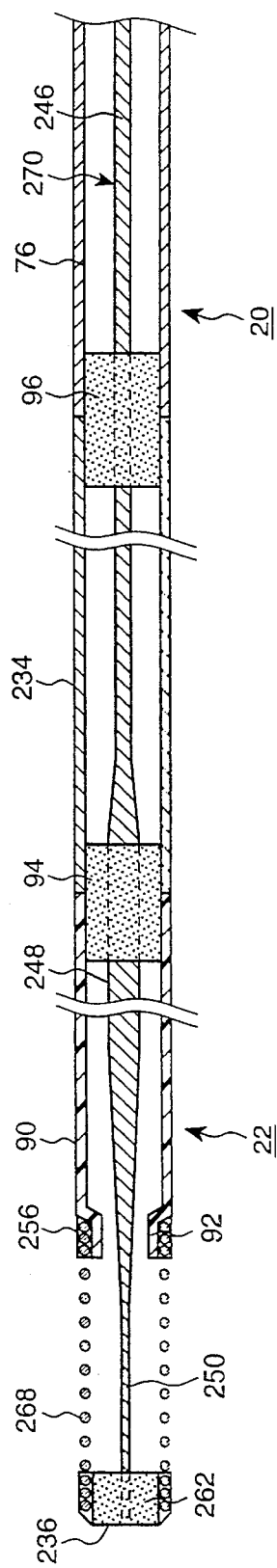
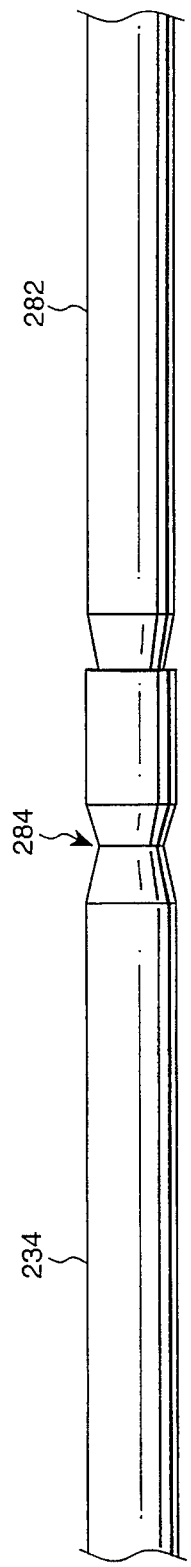
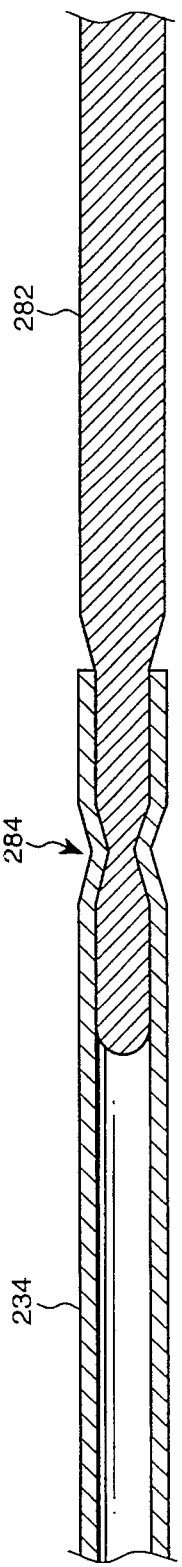
FIG. 12
FIG. 13A
FIG. 13B

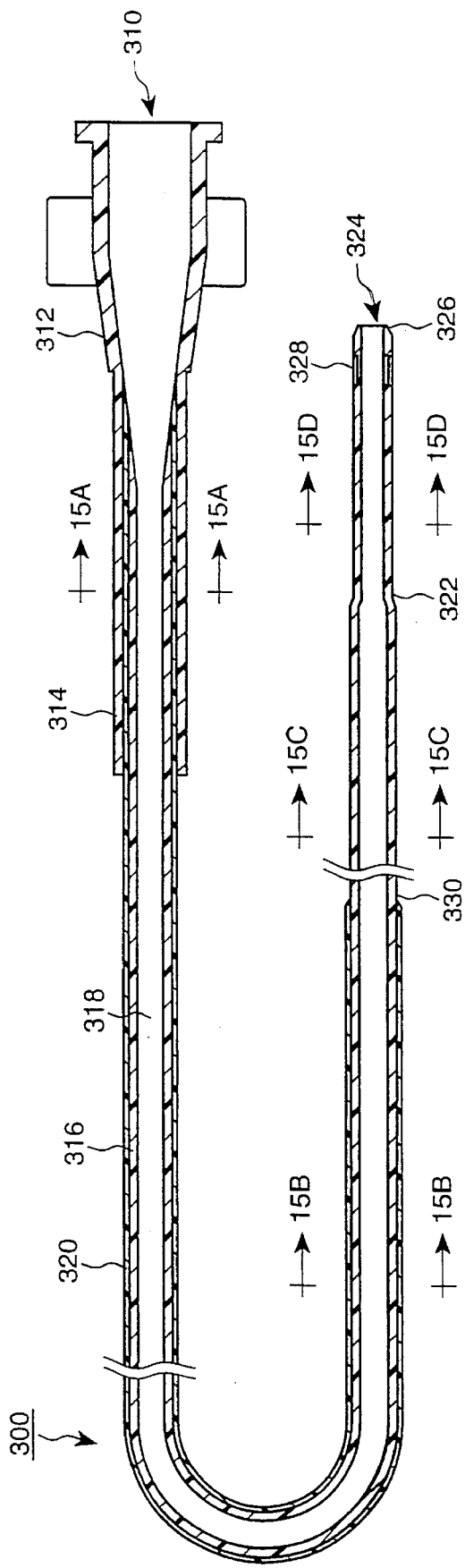
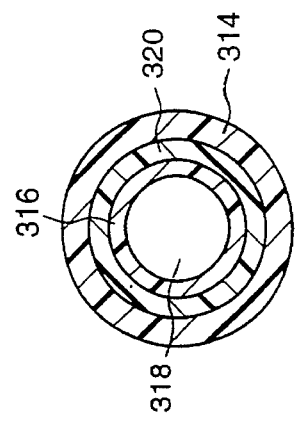
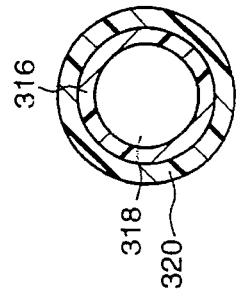
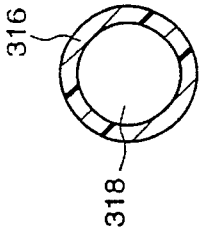
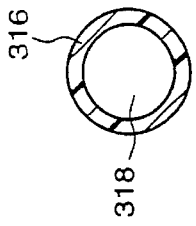

FIBER OPTIC GUIDE WIRE AND SUPPORT CATHETER THEREFOR

RELATED APPLICATIONS

This application is a continuation-in-part of application Ser. No. 07/930,934, filed Aug. 18, 1992, now abandoned.

BACKGROUND OF THE INVENTION

1. Field of the Invention

The present invention relates to guide wires and catheters used for surgical operations, and more specifically, to catheters such as fiber optic catheters used for illuminating and ablating intravascular regions and to guide wires for positioning such catheters.

2. Description of the Related Art

Angioplasty, a therapeutic medical procedure in which a catheter or the like is inserted into a blood vessel to increase blood flow, has developed in many cases as a safer, less expensive alternative to by-pass surgery. The first catheters for angioplasty were balloon catheters built up around a steerable guide wire core. The catheter is inserted into the vessel until the position of the balloon corresponds to the position of an obstruction in the blood vessel, and then the balloon is pressurized, opening the artery and increasing blood flow.

Typically, a steerable guide wire passes through the balloon catheter and is able to move independently of the catheter. The guide wire, of relatively small diameter, is inserted into the patient's blood vessel and moved into proper position past the obstruction. Then the balloon catheter, surrounding the guide wire, is advanced along the guide wire until the catheter is in proper position, with the balloon at the obstruction. This guide wire and catheter combination allows the guide wire to be inserted into place before the catheter thus making it easier to position the catheter.

Catheters containing optical fibers have also been constructed for insertion into veins and arteries. Energy is conducted along the fibers to irradiate internal parts of the body for diagnostic and surgical purposes. There are also many other medical applications in which it is desirable to deliver energy, such as laser energy, through an optical fiber or similar waveguide device disposed in a body cavity for treatment or diagnosis. These include the ablation of tissue such as plaque (e.g., angioplasty) and tumors, the destruction of calculi and the heating of bleeding vessels for coagulation. The lasers used may produce either pulsed or continuous-wave light of wavelengths ranging from the ultra-violet to the infra-red. Like balloon catheters, laser catheters are generally used with a guide wire to steer and position the catheter in the patient's body.

Laser and balloon techniques may be combined in an angioplasty process. An example of such a technique is given in U.S. Pat. No. 4,834,093 to Littleford et al. In this patent, a laser catheter is introduced into an intravascular area with the aid of a guide wire. The catheter/guide wire combination is positioned near a vascular occlusion, and the catheter is used to deliver laser energy to the occlusion to ablate a channel through the occlusion. While leaving the guide wire in position, the laser catheter is withdrawn from the patient and a balloon catheter is slid down the guide wire to the treatment site. The balloon catheter is inflated to dilate the remaining occluded area. When the catheter and guide wire are withdrawn, the previously occluded area remains dilated; thus, blood flow through the region is increased.

U.S. Pat. No. 4,854,315 to Stack et al. shows a laser catheter employing a related technique. In the Stack et al. device, a guide wire is used to position a first laser catheter near an intravascular obstruction. The first catheter is used to ablate a channel through the obstruction and to better position the device within the vessel. A second, larger catheter concentrically disposed on the first catheter is slid down the first catheter/guide wire assembly to the obstruction and continues the ablation process by eliminating the peripheral regions of the obstruction. In this manner, a level of blood flow comparable to that achieved through balloon dilation may be realized.

U.S. Pat. No. 4,739,768 to Engelson discloses an infusion catheter usable in conjunction with a guide wire. The catheter has a relatively stiff inner proximal member and a more flexible outer member covering at least a portion of the inner member and projecting therefrom at its distal end. The bifurcated stiffness profile of the infusion catheter aids in the tracking and placement of a conventional guide wire threaded therein.

In the above prior art designs, the shape and nature of the vascular occlusion will not always permit a guide wire to be positioned so that a laser catheter can be accommodated for ablation. A total vascular occlusion may prevent a guide wire from crossing the occlusion. If the occlusion cannot be crossed by conventional techniques, such as dottering the wire through the occlusion, by-pass surgery is required to reestablish blood flow through the vessel.

Though a laser catheter can ablate the occlusion and thus allow the surgical assembly to pass, its relatively large diameter prohibits adequate positioning within the vessel to perform the ablation process. Moreover, the large size of the guide wire/catheter combination may traumatize some vessels or otherwise limit the use of the device.

SUMMARY OF THE INVENTION

It is an object of this invention to provide a guide wire which is capable of delivering laser energy to intravascular areas.

It is another object of the present invention to provide a guide wire capable of crossing total occlusions in blood vessels.

It is yet another object of the present invention to provide a guide wire which can perform preliminary ablation for a laser catheter.

It is still another object of the present invention to provide a laser ablation device that will not traumatize small vessels.

It is yet a further object of the present invention to provide a steerable, torquable laser ablation device that is capable of being shaped to traverse vascular regions.

It is a further object of the present invention to provide a system and method of exchange that permits a proximal coupler to be removed from a laser guide wire while the guide wire remains in place in a patient, thereby permitting the laser guide wire to be used as a conventional guide wire for a laser, balloon or other type of catheter.

It is another object of the present invention to provide a device for laser ablation which does not produce clinically significant perforations.

It is yet another object of the present invention to provide a support catheter for aiding placement in a patient's body of a guide wire or laser ablation device as described above.

The above objects are achieved by providing a guide wire having a tubular portion with a flexible body fixed to its distal end. The distal end of the body may be composed of a material more radiopaque than its proximal portion. Optical fibers are disposed within the assembly and terminate in a radiopaque tip at the distal end of the body.

The guide wire may have a longitudinal marker wire for providing stiffness and radioscopic tracking characteristics, or it may include a mandrel which, in addition to those features, also aids in tip shaping and transmission of torque along the guide wire. The guide wire has a proximal end attached to the tube and a distal end that also terminates in the tip.

The invention may be maneuvered and positioned in a vascular area like a conventional guide wire using a torque transmitting device and may be used in conjunction with a support catheter to provide advantageous maneuverability characteristics. Then, laser energy from a laser light source at a proximal end of the guide wire is conveyed to the vascular area by the optical fibers to ablate an obstruction. Once the guide wire has ablated a passage in the obstruction, it may be placed in the passage and its proximal end severed from the proximal mount. The exchange mechanism or torque device may then be slid off the severed end to leave the guide wire portion. A larger treatment catheter may then be slid over the guide wire as if it were a conventional guide wire to continue the ablation operation. Additionally, other treatment catheters may be freely loaded on and off the guide wire as needed.

Employing polymer tubing, a wire coil, or a combination thereof for the distal body, the guide wire may be used in peripheral or coronary angioplasty applications.

BRIEF DESCRIPTION OF THE DRAWINGS

These and other objects and advantages of this invention will become apparent and more readily appreciated from the following description of the presently preferred exemplary embodiments, taken in conjunction with the accompanying drawings, of which:

FIG. 1 is a perspective view of a fiber optic guide wire according to the present invention;

FIG. 2A is an enlarged longitudinal cross-sectional view of a guide wire tip according to a first embodiment of the present invention;

FIG. 2B is an enlarged axial cross-sectional view taken along the 2B—2B line of FIG. 2A;

FIG. 6A is an enlarged partial longitudinal cross-sectional view of the guide wire tip according to a second embodiment of the present invention.

FIG. 6B is an enlarged axial cross-sectional view taken along the 6B—6B line of FIG. 6A;

FIG. 7 is an enlarged longitudinal partial cross-sectional view of a guide wire according to a third embodiment of the present invention;

FIGS. 9A and 9B are perspective and cross-sectional views, respectively, of a torque knob according to the present invention;

FIG. 12 is an enlarged longitudinal cross-sectional view of a distal portion of the guide wire of FIG. 8;

FIGS. 13A and 13B are perspective and cross-sectional views, respectively, of a guide wire according to the present invention used with a doc wire;

FIG. 14 is a longitudinal cross-sectional view of a support catheter according to the present invention; and FIGS. 15A–15D are axial cross-sectional views of the support catheter of FIG. 11.

DETAILED DESCRIPTION OF THE PRESENTLY PREFERRED EXEMPLARY EMBODIMENTS

Figure 3:
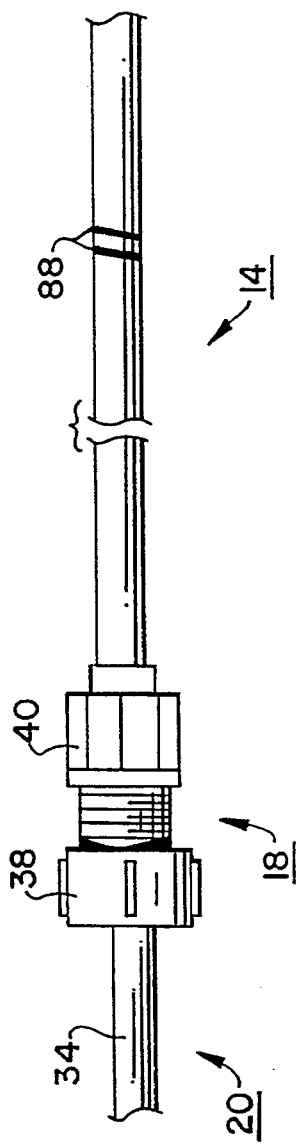
FIG. 3 is a perspective view of an exchange mechanism of a guide wire according to the present invention.

FIG. 1 depicts a perspective view of a fiber optic guide wire 10 according to the present invention. A proximal end 12 of a light conveying cable 14 is connected to a proximal mount 16 which can be coupled to a source of radiant energy. While any suitable coupling device may be used, the proximal mount described in U.S. Pat. No. 07/899,470 to Nielson et al. (incorporated herein by reference) is preferred for this purpose.

The light conveying cable 14 is plastic tubing and has optical fibers disposed within, and these fibers are affixed to proximal mount 16 using techniques known in the art. A second end of light conveying cable 14 is attached to exchange mechanism 18, which will be described more fully herein.

The distal side of exchange mechanism 18 is connected to guide wire assembly 20. The distal end of guide wire assembly 20 is terminated by tip 22, which will be described more fully herein.

FIGS. 2A and 2B are cross-sectional views of a first embodiment of the guide wire assembly 22 of FIG. 1. The internal structure of the guide wire assembly 22 is clearly illustrated in this drawing. Guide wire assembly 22 comprises optical fiber bundle 24 disposed within jacket 26. The bundle may comprise, for example, 12–90 polyimide-buffered fibers each approximately 45–100 μm in diameter (of course, for larger fiber diameters, fewer fibers should be used), and the jacket may be made from any suitable material; for example, a polyester copolymer tubing such as Hytrel 82D has proven to be advantageous in this application. Jacket 26 may additionally be coated with a suitable lubricant. An ultraviolet-curable hydrophilic coating manufactured by Bio-Metric Systems, Incorporated is advantageously employed for this purpose.

The distal tip 22 of guide wire assembly 20 comprises marker band 28. Marker band 28 is advantageously made from a radiopaque material such as platinum-iridium and includes a proximal end 30 with a reduced outer diameter. The reduced outer diameter portion 30 of marker band 28 is disposed between jacket 26 and optical fiber bundle 24 and is bonded with these components using a suitable adhesive such as Loctite 454 in a manner more fully described below. The distal rim of marker band 28 may be beveled at an angle ø to give the catheter tip a less traumatic profile, thus enabling the tip to pass through vascular channels more easily. A bevel angle ø of sixty degrees from the face of the marker band has been found to provide good results.

Additionally, the distal end of the optical fiber bundle 24 may be potted within the marker band 28 using a glue plug, and the portion of the glue plug proximate to the marker band 28 may also be beveled at a sixty degree angle.

Also, the terminal face 36 of the optic fiber bundle 24 may also be beveled to provide a smooth transitional area. To avoid massive internal reflection within the optical fiber bundle 24, the bevel angle of the fibers should be no more than 23°.

Longitudinal marker wire 32 also runs within jacket 26. A distal end of longitudinal marker wire 32 is attached to a proximal end of marker band 28. Like marker band 28, longitudinal marker wire 32 is fabricated from a radiopaque material such as platinum so that the distal tip 22 of guide wire assembly 20 will be easily detectable by radioscopic diagnostic techniques. Additionally, longitudinal marker wire 32 adds stiffness to the hypo tube to jacket transition to aid in tracking the guide wire through tortuous vascular passages.

The proximal end of jacket 26 is bonded to the distal end of hypo tube 34. The proximal end of hypo tube 34 is coupled to exchange mechanism 18 Hypo tube 34 is preferably constructed of stainless steel. Preferably, it is provided with a low-friction substance on its exterior surface such as Teflon® or a similar lubricant.

Longitudinal marker wire 32 extends through and is fixed to the proximal end of hypo tube 34. Thus, longitudinal marker wire 32 increases the structural integrity of the guide wire by providing a strong connection between marker band 28 and the remainder of the guide wire should marker band 28 accidentally become disengaged from jacket 26 and optical fiber bundle 24.

It should be noted that the relative dimensions of the components of guide wire assembly 20 have been exaggerated for demonstration purposes. For peripheral angioplasty applications, jacket 26 is preferably approximately 8–12 cm in length, while hypo tube 34 preferably has a length of approximately 137 cm. Also, jacket 26 and hypo tube 34 preferably have an outer diameter of approximately 0.033 in. and an inner diameter of approximately 0.024 in.

As shown in FIG. 3, a proximal end of hypo tube 34 is attached to a distal side of exchange mechanism 18. Hypo tube 34 having optical fiber bundle 24 disposed therein enters exchange mechanism 18 through cap 38 of a Tuohy-Borst connector. Light conveying cable 14 enters exchange mechanism 18 through body 40 of the Tuohy-Borst connector and is coupled to hypo tube 34 as described below. Marking 88 on the exterior surface of light conveying cable 14 indicates the proximal end of an exchange lead (not shown) as will be more fully described below.

Figure 4:
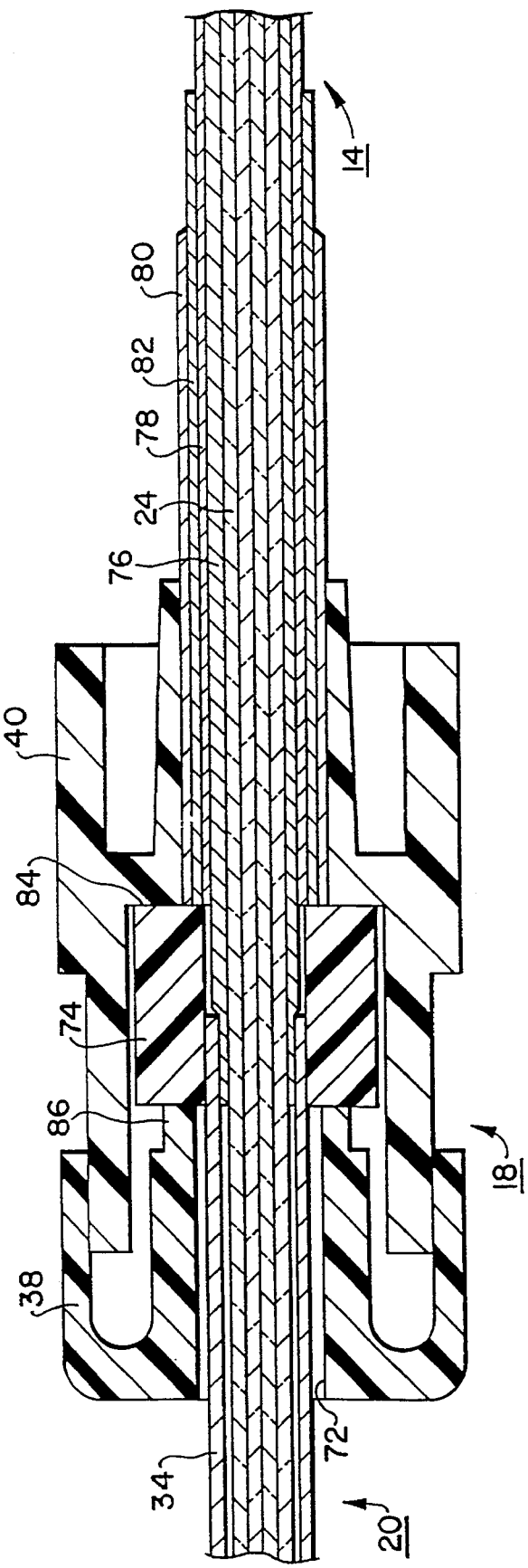
FIG. 4 is an enlarged longitudinal cross-sectional view of the exchange mechanism of FIG. 3.

FIG. 4 is a longitudinal cross-sectional view of exchange mechanism 18 which more clearly shows the coupling of hypo tube 34 to light conveying cable 14. Hypo tube 34 enters exchange mechanism 18 through a hole 72 in Tuohy-Borst connector cap 38. The proximal end of hypo tube 34 terminates within ring 74 (preferably a silicone ring), and the distal end of exchange lead 76 terminates within and is bonded to the proximal end of hypo tube 34. The proximal portion of exchange lead 76 exterior to ring 74 is encased by tail tube 78 and extends approximately 100 cm on the proximal side of Tuohy-Borst body 40. Tail tube 78 also serves as the exterior of light conveying cable 14. The distal end of tail tube 78 is itself encased in two layers 80 and 82 of heat shrinkable material which serve as a strain relief for light conveying cable 14. Optical fiber bundle 24 runs through the central lumen formed by the hypo tube-exchange lead assembly.

Ring 74 seats within Tuohy-Borst connector body 40 on a face 84 perpendicular to its longitudinal axis. Cap 38 fits on the distal end of body 40 by way of screw threads, for example. Cap 38 is fitted onto body 40 so that the proximal end of collar 86 of cap 38 presses against ring 74. Thus, ring 74 is compressed along its longitudinal axis, thereby maintaining the position of exchange mechanism 18 along hypo tube 34.

The proximal end of tail tube 78 and optical fiber bundle 24 extend beyond the proximal end of exchange lead 76 and terminate in proximal mount 16. Connection of tail tube 78 and optical fiber bundle 24 may be accomplished using techniques disclosed in the above-referenced U.S. Pat. No. 07/899,470 to Nielson et al. The point along tail tube 78 where exchange lead 76 terminates may be indicated with an appropriate marking 88 (FIG. 3). Marking 88 is useful when using guide wire 10 to position a catheter as described below.

A method of making a first embodiment of the present invention will now be described. First, hypo tube 34 must be prepared for assembly. Each end of a 0.033" outer diameter, 0.028" inner diameter, 138 cm length hypo tube is sanded flat. Then, each end is reamed to 0.028". Each end is then tapered by evenly sanding it at an angle. In this tapering process, the outer diameter of the tube should be reduced by approximately 0.0005" at the terminal face of the tube end. Then, the hypo tube should be rinsed and dried.

Next, jacket 26 is prepared. A length of 0.027"×0.033" Hytrel tubing is wiped with an isopropyl alcohol-soaked Kimwipe. The tubing is cut into 25 cm lengths and fitted on a 0.024" mandrel that has been deburred, cleaned and coated with Dow 360 silicone oil. Alternatively, a Teflon-coated mandrel may be used; in this case, the silicone oil is not necessary. Approximately 5 cm of tubing should extend beyond one end of the mandrel. The assembly is then placed in a hot box set to provide a 2 psi air supply at 550° F. While firmly holding the assembly, the portion of the tubing extending beyond the mandrel is tensioned with tweezers until it looses its elasticity. While maintaining tension on the tube, the assembly is then removed from the hot box and allowed to cool. After the tube is cooled, tension on the tube is released and the hytrel tubing is removed from the mandrel. The previously-tensioned portion of the tube is cut at an angle to facilitate the insertion of 5 mm of the tubing or more into one end of the prepared hypo tube. At this stage, the outer diameter of the necked portion (i.e., the proximal end) should be approximately 0.027" or 0.0275". A razor blade is used to make a perpendicular cut on the distal end of the tube to give the tube a total length of between 8.0 cm and 12.0 cm.

Next, longitudinal marker wire 32 is prepared. A length of 0.003" diameter, 90% platinum –10% nickel wire is flattened. While taking care not to kink the flattened wire, it is cut into 155 cm lengths and set aside for later use.

Next, exchange lead 76 is prepared. A cleaned, deburred 0.024" outer diameter×1' length mandrel is wiped with a Kimwipe soaked in silicone oil. Alternatively, a Teflon-coated mandrel may be used; in this case, the silicone oil is unnecessary. A 2' length of Hytrel tubing is cut into 15 cm lengths and an end of one of the cuttings is placed over the mandrel so that approximately 2" of the tube extends beyond the mandrel. A hot box is then used to form the tubing to the mandrel in a process similar to that in the jacket fabrication described above. When the assembly is removed from the hot box, the mandrel is partially pulled out of the tubing and the tubing is cut to provide a square tapered end of approximately 1 cm fitting on the mandrel. This process will form the proximal end of exchange lead 76. The distal end of exchange lead 76 is prepared in a similar manner; however, as with jacket 26, the distal end of exchange lead 76 is cut at an angle to facilitate insertion into hypo tube 34. Once the distal end of exchange lead 76 has been prepared, the mandrel is removed and exchange lead 76 is wiped with an alcohol-soaked Kimwipe.

Next, tail tube 78 and the Tuohy-Borst connector assembly are fabricated. A length of Raychem RNF 100 3/32" shrink tubing is cut into a 2 cm and a 2.5 cm length. Hytrel 82D tubing having an outer diameter of 0.058" and an inner diameter of 0.038" is cut to a length of 88 inches. A 0.036"ø teflon coated mandrel is inserted into the tail tube. The 2.5 cm shrink tube 82 is placed on one end of tail tube 78 and heat is applied to fix shrink tubing 82 on tail tube 78. The 2 cm shrink tube 80 is similarly shrunk onto the 2.5 cm length 82. A 0.25" outer diameter, 0.052" inner diameter, 0.25" wide silicone ring 74 is placed in Tuohy-Borst connector body 40 and cap 38 is then snapped and screwed onto body 40. A ring of EP30HT epoxy is deposited around the edge of shrink tube 80 and the end of the shrink tube/tail tube assembly is inserted into connector body 40 with a twisting motion to spread the epoxy along the interior surfaces of the connector body 40 contacting shrink tubing 80. The assembly is then allowed to cure.

Next, optical fiber bundle 24 is formed. Twelve to ninety spools of 45–100 μm diameter optical fibers are loaded on a fiber pulling rack. Approximately four meters of fibers are pulled from the rack along a clean, planar surface. The fibers are then cut from the pulling rack using a cutting stone.

The above-described components are then assembled together to form the laser guide wire. First, optical fiber bundle 24 is inserted into the proximal end of hypo tube 34. Approximately 20 cm of the fibers should extend beyond the distal end of hypo tube 34. This portion of the fibers is inserted into the proximal end of jacket 26 so that approximately 5 cm of the fibers extend beyond the distal end of jacket 26. Longitudinal marker wire 32 is inserted into the distal end of jacket 26 until the proximal end of wire 32 appears at the proximal end of jacket 26 and then positioned so that approximately 1 cm of longitudinal marker wire 32 extends beyond the distal end of jacket 26. The marker wire is inserted into the hypo tube until it extends out of the proximal end of the hypo tube. Then the jacket is inserted into the hypo tube. The jacket/marker wire assembly is then moved toward hypo tube 34 so that the marker wire 32 and the proximal end of jacket 26 are inserted into hypo tube 34. Marker wire 32 should be substantially parallel to the longitudinal axis of the hypo tube/jacket assembly with no twists. Jacket 26 is then retracted from hypo tube 34 and its proximal end is coated with epoxy and reinserted into hypo tube 34. Excess epoxy is wiped away and the assembly is cured. The proximal end of longitudinal marker wire 32 extending beyond the proximal end of hypo tube 34 is trimmed to length.

Exchange lead 76 is then slid over the proximal end of optical fiber bundle 24 so that the proximal portion of longitudinal marker wire 32 is sandwiched between the exterior of the angled, tapered end of exchange lead 76 and the interior surface of hypo tube 34. Exchange lead 76 is backed out of hypo tube 34, and exchange lead 76 and the end of hypo tube 34 are wiped with an alcohol-soaked Kimwipe. A ring of epoxy is deposited on the end of exchange lead 76 and it is reinserted into hypo tube 34. Excess epoxy is wiped away.

The assembly is then cured. Curing of the exchange lead/hypo tube bond may be performed concurrently with curing of the jacket/hypo tube bond to speed the fabrication process. The distal end of longitudinal marker wire 32 is trimmed so it extends only 1 mm beyond the distal end of jacket 26, and the 1 mm end of the marker wire is fitted on the reduced diameter of the marker band 28. Reduced outer diameter portion 30 is coated with cyanoacrylate adhesive and inserted into the lumen defined by jacket 26 so that it is sandwiched between the exterior of optical fiber bundle 24 and the interior surface of jacket 26. The assembly is cured, and excess adhesive is removed.

The distal end of optical fiber bundle 24 may then be potted, beveled and polished using techniques known in the art. An advantageous method is described in U.S. Pat. No. 5,263,952 to Grace et al., incorporated herein by reference. The proximal end of fiber bundle 24 is inserted into cap 38 of the Tuohy-Borst connector, the Tuohy-Borst assembly is moved distally and then tightened over the hypo tube/distal exchange section. The proximal ends of tail tube 78 and optical fiber bundle 24 may be connected to proximal mount 16 as described in the above-referenced application 07/899, 470 to Nielson et al.

Guide wire 10 may be advantageously used to ablate an intravascular occlusion and then to position a catheter for subsequent occlusion. In this technique, guide wire 10 is connected to a source of light energy such as a laser by way of proximal mount 16. Guide wire assembly 20 is partially inserted into a patient using conventional surgical techniques and positioned so tip 22 is proximate to the occlusion. Energy transmitted from the source along optical fiber bundle 24 to tip 22 may then be used to ablate a channel through the occlusion.

Once a channel has been formed in the occlusion, tip 22 is positioned within the channel. Light conveying cable 14 is severed where marking 88 indicates the termination of exchange lead 76. Tuohy-Borst cap 38 is disengaged from body 40, and both pieces are slid off the proximal end with tail tube 78 and shrink tubes 80 and 82. The proximal end of newly-severed optical fiber bundle 24 is pulled away from exchange lead 76 and then cut so that bundle 24 retracts inside exchange lead 76. Then, a catheter may be placed on the proximal end of exchange lead 76 and slid down to the entry point of hypo tube 34 in the patient's body. The catheter is then introduced into the patient's body and slid along hypo tube 34 until it is proximate to the partially-ablated occlusion. With this procedure, a laser catheter may be used to ablate a larger area of the occlusion. A balloon catheter may be used to dilate the vascular area having the occlusion instead of a laser catheter.

Figure 5:
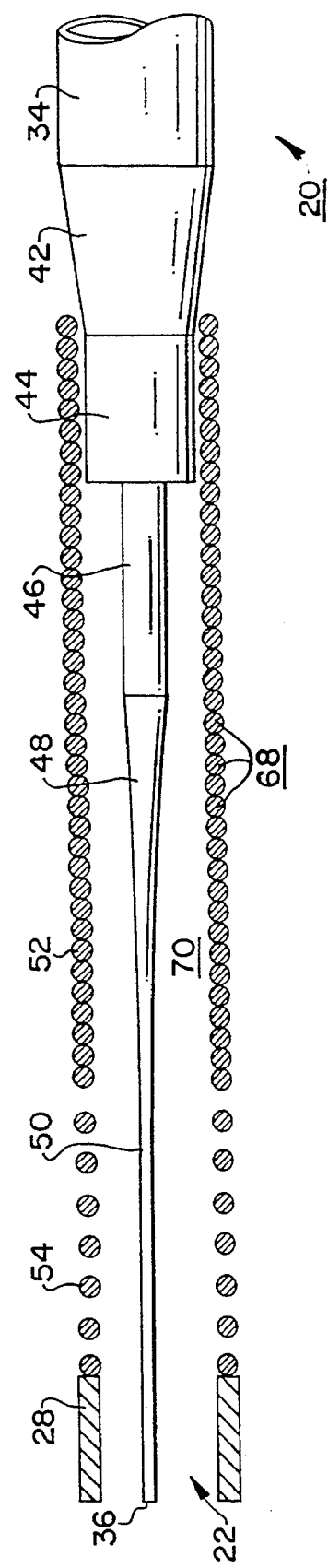
FIG. 5 is an enlarged longitudinal cross-sectional partial view of a guide wire section according to a second embodiment of the present invention.

FIG. 5 is a partial longitudinal cross-sectional view of a second embodiment of the guide wire assembly 10 of FIG. 1. From hypo tube 34 in the proximal direction, this embodiment is the same as that described relative to FIGS. 3 and 4. However, this embodiment differs from the previous embodiment distal to hypo tube 34. In FIG. 5, optical fiber bundle 24 has been removed to more clearly show the internal structure of guide wire assembly 20. Instead of using a polymer jacket on the distal end of hypo tube 34, this embodiment employs helical, radiopaque coil 68 to form the distal end of guide wire assembly 20. Hypo tube 34 includes an intermediate tapered portion 42 connected to a reduced diameter portion 44 on its distal end. Hypo tube 34 is preferably constructed from stainless steel and, proximal to tapered portion 42, has an outer diameter of approximately 0.018 in. and an inner diameter of approximately 0.013 in. Also, hypo tube 34 may be coated to provide a low-friction surface for improved guide wire maneuverability characteristics. A suitable coating for this purpose is Teflon®.

Coil 68 has a proximal end covering and connected to the reduced diameter portion 44 of hypo tube 34 and a distal end which is fixed to marker band 28. Coil 68 is preferably fabricated from a radiopaque material such as platinum so the guide wire may be tracked using radioscopic techniques as described above. Coil 68 has a proximal compressed portion 52 and a distal expanded portion 54. By stretching distal expanded portion 54 of coil 68, the distal end of guide wire assembly 22 can better track vascular contours while compressed portion 52 provides rigidity to the structure.

It has been found that a coil fabricated from a 90% platinum—10% nickel alloy having a wire diameter of 0.0025 in. is suitable for this purpose and additionally provides desirable flexibility, torquability and pushability characteristics. Preferably, expanded portion 54 of coil 68 is approximately 3 cm in length, while compressed portion 52 of coil 68 is approximately 27 cm in length. Also, marker band 28 is preferably fabricated from a 90% platinum—10% iridium alloy and has an outer diameter of approximately 0.018 in., an inner diameter of approximately 0.013 in., and a length of approximately 2 mm.

Mandrel 70 is mounted on an inner surface of reduced diameter portion 44 of hypo tube 34 and provides additional rigidity, torquability and pushability to guide wire assembly 20. Mandrel 70 has a proximal portion 46 eccentrically bonded to hypo tube 34 and an intermediate portion 48 which tapers down to a flattened portion 50 at its distal end. Mandrel 70 is angled so that the distal end of flattened portion 50 is substantially central to and coterminal with terminal face 36.

Preferably, mandrel 70 is fabricated from stainless steel, with the proximal portion 46 thereof having a diameter of approximately 0.005 in. and a length of approximately 15 cm, the intermediate tapered portion 48 thereof having a length of approximately 10 cm, and the flattened portion 50 thereof having a width of approximately 0.006 in., a thickness of approximately 0.002 in. and a length of approximately 3 cm.

FIGS. 6A and 6B are cross-sectional views of the second embodiment of the invention showing the placement of optical fiber bundle 24. Optical fiber bundle 24 emerges from reduced diameter portion 44 of hypo tube 34 and extends to terminate at the distal end of a glue plug 62 in marker band 28. In this embodiment, optical fiber bundle 24 is preferably comprised of a bundle of approximately 9–33 polyimide-buffered optical fibers each having a diameter of about 30–61 (most preferably, 45) μm.

The proximal end of coil 68 is attached to hypo tube 34 by solder joint 56. Similarly, a joint 60 is used to attach the distal end of coil 68 to marker band 28. The joint 60 may be a solder joint, an adhesive joint, a fused joint combining adhesive and heat, or the like. Preferably, the joint 60 is an adhesive or fused joint. A central joint 58 (preferably an adhesive or fused joint, although other joints, such as a solder joint can be employed) bonds the interface between compressed portion 52 and expanded portion 54 of coil 68 to mandrel 70. While the first two of the above-mentioned joints are annular in shape, central joint 58 is essentially disk-shaped, since the molten solder tends to flow between cracks in the coil turns and wick throughout the optical fiber bundle 24 in that region.

A method of making the second embodiment of the present invention will now be described. First, coil 68 is formed and its distal portion is stretched approximately 50% to form expanded portion 54, while the remainder of coil 68 forms compressed portion 52. Proximal portion 46 of mandrel 70 is bonded to reduced diameter portion 44 of hypo tube 34. Then, the proximal end of coil 68 is fitted over the reduced diameter portion 44 and soldered thereto. Marker band 28 is soldered to the distal end of coil 68. Optical fiber bundle 24 is inserted into the jacket/hypo tube assembly so that its distal end protrudes from marker band 28. Coil interface solder joint 58 is then formed by flowing solder at the transition between the compressed portion 52 and the expanded portion 54 of coil 68 and into optical fiber bundle 24 to bond with mandrel 70. Finally, a suitable adhesive is wicked up the distal end of optical fiber bundle 24 to form glue plug 62 within marker band 28 and terminal face 36 is polished to provide an optically smooth surface. Also, the periphery of terminal face 36 may be bevelled as described above.

After the distal end of guide wire assembly 20 has thus been fabricated, the remainder of the device may be constructed in a manner similar to the one previously described in the construction of the first embodiment of the present invention.

It has been found that a guide wire according to the second embodiment of the present invention is particularly well-suited to applications such as coronary angioplasty. In such applications, hypo tube 34 and coil 68 are together preferably approximately 175 cm long. Thus, hypo tube 34 in this embodiment is longer than that of the first embodiment, which is preferably used in peripheral angioplasty applications. Since both techniques generally introduce the guide wire into the patient's body at the groin area, additional length is required in the coronary version to reach the more distantly located vessels near the heart.

FIG. 7 depicts a portion of a third embodiment of the present invention. In this Figure, hypo tube 134 is shortened to provide a small fitting for connecting coil 68 to jacket 64, which substantially replaces hypo tube 34 in the second embodiment. Construction of this embodiment is similar to that of the second embodiment; however, the proximal end of hypo tube 134 is attached to jacket 64 with a suitable adhesive such as cyanoacrylate.

The second and third embodiments of the present invention can be used in a manner similar to that described above for the first embodiment.

Figure 8:
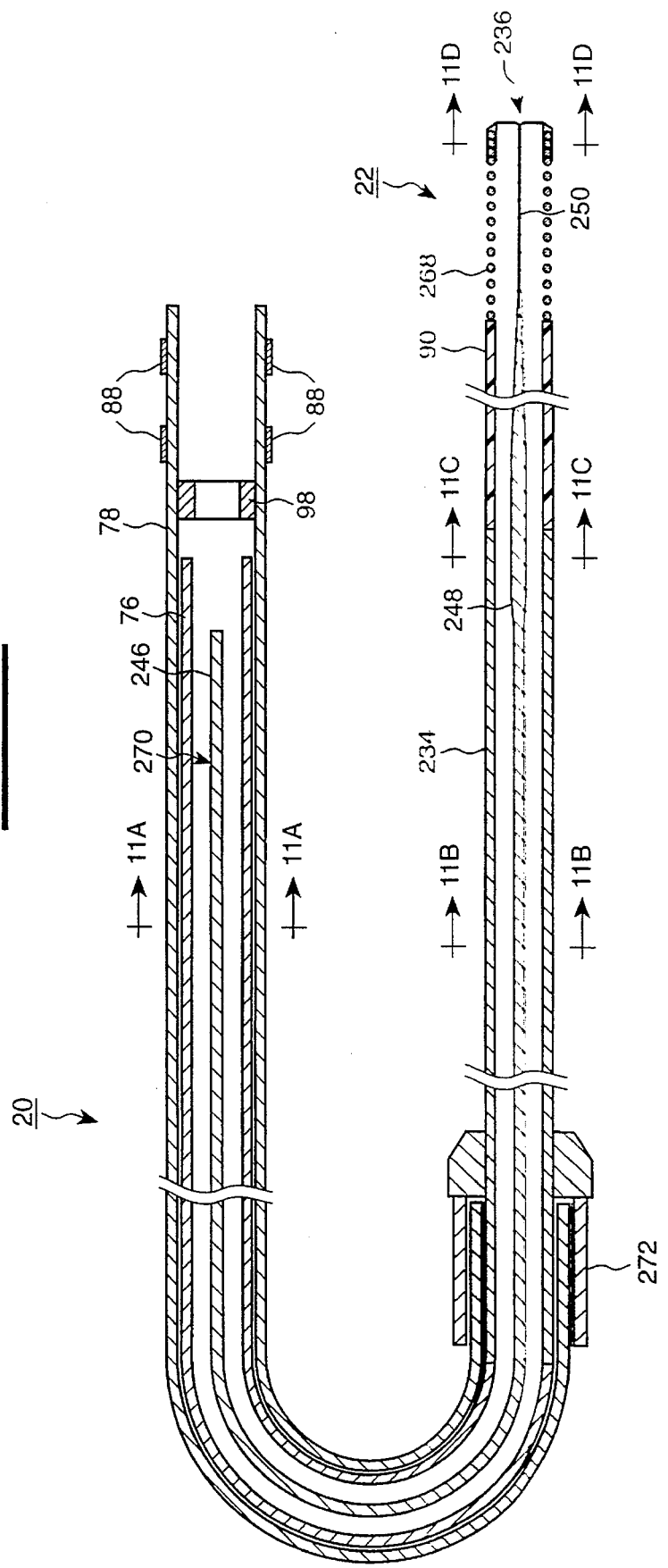
FIG. 8 is a longitudinal cross-sectional view of a guide wire according to a fourth embodiment of the present invention.

FIG. 8 is a partial longitudinal cross-sectional view of a fourth embodiment of the guide wire assembly 10 of FIG. 1, and a detailed cross-sectional view of the distal end of this embodiment is shown in FIG. 12. From exchange lead 76 in the proximal direction, this embodiment is the same as that described relative to the first, second and third embodiments; however, the distal portion differs from those aforementioned embodiments. In FIGS. 8 and 10, optical fiber bundle 224 has been removed to more clearly show the internal structure of guide wire assembly 20. Optical fiber bundle 224 is more clearly shown in FIGS. 11A–11D.

This embodiment employs a helical, radiopaque coil 268 to form the distal end of guide wire assembly 20. A distal jacket 90 having a tapered distal portion 92 fitting within the proximal end of the coil 268 extends from the distal end of a cylindrical hypo tube 234 to the proximal end of the coil 268.

The distal jacket 90 is bonded to the hypo tube 234 by a fused adhesive bond 94 and to the coil 268 by an adhesive bond 256. The proximal end of the hypo tube 234 is connected to the distal end of the exchange lead 76 with another adhesive heat bond 96.

The distal jacket 90 is preferably constructed from a 27 centimeter length of material such as high density polyethylene (HDPE) and is approximately 0.018" OD and 0.013" ID. Coil 268 is approximately 3 centimeters long with an 0.018" OD and is preferably fabricated from a radiopaque material such as a 90% platinum—10% nickel alloy having a wire diameter of 0.0025 in. so the guide wire may be tracked using radioscopic techniques as described above. Hypo tube 234 is preferably constructed from a 145 centimeter length of stainless steel and has an outer diameter of approximately 0.018 in. and an inner diameter of approximately 0.013 in.

To improve the maneuverability of the guide wire assembly 20, the coil 268 and the distal jacket 90 may be coated with a lubricous hydrophilic coating. Also, hypo tube 234 may be coated with Teflon® to reduce friction.

Mandrel 270 is fixed in place relative to the coil 268, distal jacket 90, hypo tube 234 and exchange lead 76 and provides additional rigidity, torquability and pushability to guide wire assembly 20. Mandrel 270 has a proximal portion 246 extending from the proximal end of exchange lead 76 and an intermediate portion 248 having tapered portions at each end so that the intermediate portion 248 enhances the stiffness profile and trackability characteristics of the distal end of the guide wire assembly 20. A flattened distal portion 250 of mandrel 270 extends to a distal face 236 of the guide wire assembly 20 and is bonded to a distal end of the coil 268 with an epoxy glue plug 262.

Preferably, mandrel 270 is fabricated from stainless steel, with the proximal portion 246 thereof having a diameter of approximately 0.005 or 0.006 in., the intermediate tapered portion 248 thereof having a diameter of about 0.008 in. and the flattened portion 250 thereof having a width of approximately 0.006 in., a thickness of approximately 0.0025 in. and a length of approximately 3 cm. The flattened portion 250 has a rectangular cross-section and cooperates with the optical fibers to allow the guide wire assembly 20 to be shaped and reshaped to bend it at almost any desired angle.

In this embodiment, the Tuohy-Borst connector used in previous embodiments has been eliminated, and a torque knob 272 has been used in its place. The torque knob 272 is advantageous because it can be used to torque the guide wire assembly 20, and the Tuohy-Borst connector could not. Unlike the Tuohy-Borst connector, the torque knob 272 does not secure the tail tube 78 to the hypo tube 234, and the torque knob 272 can be positioned at almost any location along the shaft of the hypo tube 234 for ease of handling, torquing and steering during a procedure.

Figure 10A:
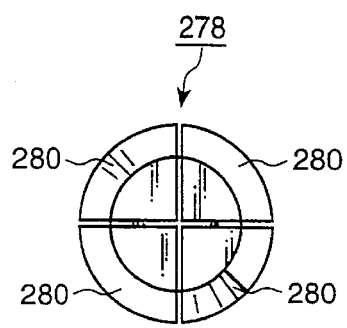
FIGS. 10A and 10B are views of an insert used in the torque knob according to the present invention.
Figure 10B:
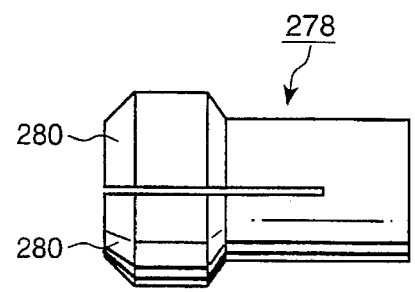
Figure 11A:
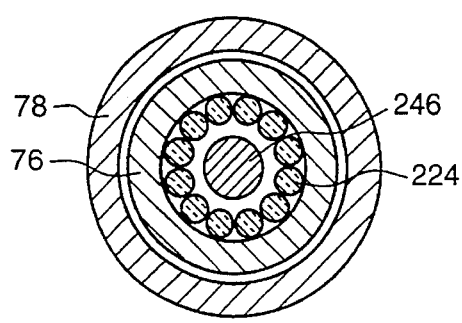
FIGS. 11A–11D are axial cross-sectional views of the guide wire of FIG. 8.
Figure 11B:
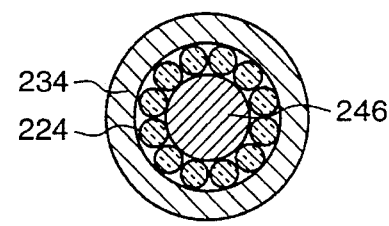
Figure 11C:
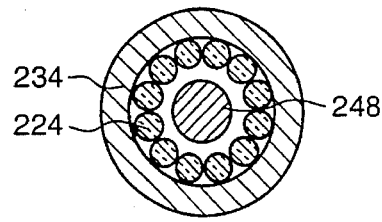
Figure 11D:
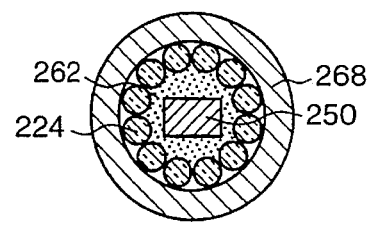

FIGS. 9A and 9B show the torque knob 272 in greater detail. The exterior of the torque knob 272 is shown the perspective view of FIG. 9A, and a cross-sectional view is shown in FIG. 9B. When cap 274 of torque knob 272 is tightened onto the body 276, the insert 278 shown in detail in FIGS. 10A and 10B is compressed and sections 280 of its distal end close around and engage hypo tube 234. Torque knob 272 then may be rotated to apply torque to the guide wire assembly 20.

FIGS. 11A–11D are cross-sectional views of the second embodiment of the invention showing the placement of optical fiber bundle 224. Optical fiber bundle 224 passes through the exchange lead 76, the hypo tube 234, the distal jacket 90, and the coil 268 and terminates at the distal face 236 of the guide wire assembly in a glue plug 262. By soldering the distal turns of the coil 268 together and using a glue plug to fix the distal ends of optical fiber bundle 224 and the mandrel 270 in place within the soldered coil portion, the marker band used in the previously-mentioned embodiments may be eliminated, thus reducing the cost of making the guide wire assembly 20. As above, the edge of the distal end 236 of the guide wire assembly 22 can be beveled to provide a less traumatic profile for the invention.

Also, the optical fiber bundle 224 may have a short (approximately 1 cm) length of shrink tube 98 encircling it between the proximal end of the exchange lead 76 and the marking 88. The shrink tube 98 retains the discarded portion of the optical fiber bundle 224 together as will be described in more detail below.

In this embodiment, optical fiber bundle 224 is preferably comprised of a bundle of approximately 9–33 polyimide-buffered optical fibers each having a diameter of 30–61 (most preferably 45) μm.

The arrangement of the distal coil and jacket assembly in this embodiment is particularly advantageous in maneuvering the guide wire 20. If the coil 268 on the jacket 90 is constricted within an artery or lesion, torque still may be transmitted from the torque knob 272 to the distal face 236 of the guide wire 20. This is because the coil and jacket combination is secured to the rest of the assembly only at the extreme distal face 236 and at its proximal end by adhesive bond 256, and the fibers and mandrel 270 are fairly loosely packed within the coil 268. When torque is applied to the guide wire 20 by the torque knob 272, it can be conveyed to the distal tip 236 via the mandrel without binding the coil and jacket combination.

This embodiment may of course be used clinically in a manner substantially similar to the previous embodiments. Although the torque knob 272 is not connected to tail tube 78 as is the Tuohy-Borst connector of the previous embodiments, removing torque knob 272 helps remove tail tube 78.

Variations on these embodiments are of course possible. For example, the exchange lead 76 may be constructed from a braided polymer material with a waffle-like surface instead of a relatively homogenous polymer material. A substantial portion of the exchange lead 76 may even be replaced by an equal or reduced diameter portion of the hypo tube.

Also, as an alternative to the methodology of clinical usage described above, a 125 cm doc wire 282 or a similar instrument may be inserted into the proximal end of the hypo tube 234 to further position the guide wire assembly 20 as shown in FIGS. 13A and 13B. FIG. 13A shows a distal portion of the doc wire 282 engaging the proximal end of the hypo tube 234. As seen in FIG. 13A and the cross-sectional view shown in FIG. 13B, the doc wire 282 is coupled to the hypo tube 234 by a crimp 284.

Preferably, the doc wire 282 is made of stainless steel or nickel-titanium and has a low friction coating such as Teflon® or Parylene® covering it. For optimal engagement with the hypo tube 234, the doc wire 282 has an outer diameter the same as or slightly smaller than the outer diameter of the hypo tube 234.

As with the second embodiment, it has been found that a guide wire according to the fourth embodiment of the present invention is particularly well-suited to applications such as coronary angioplasty. In such applications, distal jacket 90 and coil 268 are together preferably approximately 30 centimeters long. The working length (the hypotube, jacket and coil) of the guide wire 20 is then 175 cm, and the exchange section covered by the tail tubing is 125 cm, for a total length of 300 cm.

A support catheter 300 for use with a guide wire assembly 20 according to the present invention now will be described with reference to FIGS. 14 and 15A–15D. FIG. 14 is a longitudinal cross-sectional view of the support catheter according to the present invention, and FIGS. 15A–15D are axial cross-sectional views along the support catheter.

The support catheter has a proximal end 310 terminating in a female luer connector 312. A catheter body 316 extends from the distal portion of the luer connector 312 to a distal catheter end 324 and in conjunction with the luer connector 312 defines a lumen 318 therewithin. A proximal jacket 320 covers the proximal portion of the catheter body 316, and a luer leg 314 of the luer connector 312 covers the proximal end of the proximal jacket 320.

Preferably, the luer connector 312, the proximal jacket 320 and the catheter body 316 are made from HDPE. The luer connector 312 is about 10 centimeters long with a 5 centimeter overlap with the proximal jacket 320 and the catheter body 316, and the luer leg has about a 0.080" OD and a 0.050" ID. The proximal jacket is approximately 100 centimeters long with a 0.039" OD and a 0.045" ID, and the catheter body 316 preferably is approximately 130 centimeters long with a tapered portion 322 thereof being about 10 centimeters from its distal face 324 and transitioning from a proximal portion of 0.036" OD and 0.025" ID to a distal portion of 0.031" OD and 0.022" ID. In this way, the support catheter exhibits a stiffness profile that progressively decreases from the proximal end to the distal end thereof.

As noted above, the catheter body 316 has a tapered portion 322 intermediate the distal end 330 of the proximal jacket 320 and the distal end 324 of the catheter. This portion 330 preferably is tapered to impart a less traumatic profile to the support catheter when used in situ. Additionally, the distal end 330 of the proximal jacket 320 and the rim of the distal end 324 of the catheter may be tapered for similar reasons. To enhance the slidability of the support catheter 300, its distal 30 centimeters may be covered with a lubricous hydrophilic coating.

A radiopaque band 328 is disposed near the distal end 324 of the catheter to aid in fluoroscope visualization of the placement of distal end 324. Preferably, the band 328 is about 1 millimeter wide with a 0.031" OD and a 0.027" ID.

To use the support catheter with the guide wire assembly 20 according to the present invention, the guide wire 20 is inserted into the support catheter lumen 318 and advanced until catheter distal face 324 and the guide wire distal face are coterminal. The support catheter-guide wire assembly is then introduced into the patient's body using a guide catheter as is known in the art. After the catheter-guide wire assembly has passed beyond the distal end of the guide catheter, the guide wire 20 is advanced out of the support catheter to a treatment site. Once positioned, the support catheter 300 also may be advanced to the treatment site to provide additional support. During this process, the support catheter 300 may be hydrated or irrigated with saline solution through its lumen 318 before insertion of the guide wire 20 to reduce friction.

If the treatment site is occluded or obstructed to such a degree that the guide wire 20 cannot pass therethrough, the guide wire 20 is used to ablate part of the obstruction to create a passage. The distal end of the guide wire 20 is then positioned beyond the obstruction. Then, the torque knob 272 is loosened and removed. In this step, the guide wire 20 is severed to disconnect the proximal mount portion from the portion disposed in the patient's body. After this is done, removal of the torque knob 272 also aids in removal of the tail tube 78.

At this point, the proximal end of the exchange lead 76 will have a short length of optical fiber bundle 224 projecting therefrom and encircled by shrink tube 98. Tension is applied to the optical fiber bundle 224 to withdraw it from the exchange lead 76 a little more, and it is severed at the end of the exchange lead 76. With the tension released, the end of optical fiber bundle 224 retracts inside the exchange lead 76, thereby leaving a clean termination. Since fibers in the excess length of the optical fiber bundle 224 are held together by shrink tube 98, they are prevented from falling onto the patient or other undesirable places.

The support catheter 300 then is slid off the guide wire 20, and a conventional balloon or optical fiber catheter is slid on to further treat the site. The treatment catheter may be off-loaded and freely swapped with a number of other treatment catheters for additional treatment operations.

Numerous variations on the above-described technique will be readily apparent to one of ordinary skill in the art. For example, after the guide wire 20 is used to ablate a passage through a vascular obstruction, it may be removed and replaced by a differently-sized conventional guide wire. Also, although not as cost-effective, a conventional treatment catheter may be used in place of the support catheter.

The support catheter 300 according to the present invention is suitable for other applications in intravascular angioplasty. For example, the support catheter may be used as a conduit for exchanging guide wires or for maintaining position at a treatment site while a guide wire is withdrawn. That is, if a doctor wishes to reshape a guide wire currently in place, she can withdraw the guide wire through the support catheter while maintaining position with the support catheter. Once the guide wire is reshaped, it can be advanced inside the support catheter to the treatment site as described above.

Other uses of the support catheter 300 will be readily apparent to those skilled in the art. For example, by moving a support catheter over a guide wire, the position of the guide wire tip may be altered. Further, the support catheter may be used as a conduit for injecting therapeutic or diagnostic fluids. Also, the catheter may be used to cross lesions.

Although a few preferred embodiments of the invention have been shown and described, it will be appreciated by those skilled in the art that changes may be made in these embodiments without departing from the principles and the spirit of the invention, the scope of which is defined in the appended claims.

What is claimed is:

1. A fiber optic guide wire apparatus comprising:

a hollow guide wire assembly comprising a hypo tube and a hollow outer jacket, said hollow outer jacket having a proximal end connected to a distal end of said hypo tube, said hollow guide wire assembly having a distal end termination;

a plug disposed at a distal end of said hollow guide wire assembly and having a distal face flush with said distal end termination of said hollow guide wire assembly;

an optical fiber bundle disposed within said guide wire assembly and including a plurality of optical fibers, said optical fiber bundle extending through said plug and having a distal face terminating at said distal face of said plug;

said plug surrounding said optical fibers in said bundle and bonding said fibers to said distal end of said hollow guide wire assembly;

a mandrel, disposed within said guide wire assembly, having a distal end terminating at said distal end of said guide wire assembly, said mandrel cooperating with said optical fiber bundle to permit said distal end of said hollow guide wire assembly to be shaped as desired by an operator;

means for introducing light energy into a proximal end of said optical fiber bundle; and an exchange lead having a distal end connected to a proximal end of said hypo tube;

wherein a proximal end of said mandrel terminates proximate to a proximal end of said exchange lead.

2. The fiber optic guide wire apparatus of claim 1, further comprising:

a shrink tube disposed on said optical fiber bundle proximal to a proximal end of said exchange lead;

whereby said shrink tube maintains fibers in said optical fiber bundle together when said optical fiber bundle is severed between said shrink tube and said proximal end of said exchange lead.

3. The fiber optic guide wire apparatus of claim 1, wherein said mandrel comprises:

a base portion at said proximal end; and a flattened portion at said distal end.

4. The fiber optic guide wire apparatus of claim 3, wherein said mandrel further comprises an enlarged portion intermediate said base portion and said flattened portion.

5. The fiber optic guide wire apparatus of claim 4, wherein said enlarged portion is substantially coextensive with a proximal end of said outer jacket.

6. The fiber optic guide wire apparatus of claim 1, wherein said outer jacket comprises a distal jacket and a wire coil.

7. The fiber optic guide wire apparatus of claim 1, further comprising a torque knob disposed on said hypo tube, said torque knob engaging said guide wire assembly to transmit torque applied to said knob to said distal end of said guide wire assembly.

8. The fiber optic guide wire apparatus of claim 1, said apparatus further comprising:

a support catheter coextensive with and covering at least an intermediate portion of said hollow guide wire assembly.

9. The fiber optic guide wire apparatus of claim 8, said support catheter comprising:

a proximal portion having a first stiffness; and a distal portion having a second stiffness less than said first stiffness.

10. The fiber optic guide wire apparatus of claim 9, wherein:

said proximal portion includes a proximal portion of a catheter body and an outer jacket concentrically disposed around said proximal portion of said catheter body; and said distal portion includes a distal portion of said catheter body.

11. The fiber optic guide wire apparatus of claim 10, further comprising a marker band at a distal end of said support catheter.

12. A fiber optic guide wire apparatus comprising:

a hollow guide wire assembly comprising a hypo tube and a hollow outer jacket, said hollow outer jacket having a proximal end connected to a distal end of said hypo tube, said hollow guide wire assembly having a distal end termination;

a plug disposed at a distal end of said hollow guide wire assembly and having a distal face flush with said distal end termination of said hollow guide wire assembly;

an optical fiber bundle disposed within said guide wire assembly and including a plurality of optical fibers, said optical fiber bundle extending through said plug and having a distal face terminating at said distal face of said plug;

said plug surrounding said optical fibers in said bundle and bonding said fibers to said distal end of said hollow guide wire assembly;

means for introducing light energy into a proximal end of said optical fiber bundle;

a torque knob disposed on said hypo tube, said torque knob engaging said guide wire assembly to transmit torque applied to said knob to said distal end of said guide wire assembly;

an exchange lead having a distal end connected to a proximal end of said hypo tube; and a tail tube having a distal end covering at least a proximal end of said exchange lead and a proximal end connected to said means for introducing light energy;

wherein said torque knob is disposed distal to a distal end of said tail tube and may be freely slid along said hypo tube and said exchange lead to remove said tail tube.

13. A fiber optic guide wire apparatus, comprising:

a hollow guide wire assembly comprising a hypo tube, and a hollow outer jacket, said hollow outer jacket having a proximal end connected to a distal end of said hypo tube, said hollow guide wire assembly having a distal end termination;

a plug disposed at a distal end of said hollow guide wire assembly and having a distal face flush with said distal end termination of said hollow guide wire assembly;

an optical fiber bundle disposed within said guide wire assembly and including a plurality of optical fibers, said optical fiber bundle having a distal face terminating at said distal face of said plug;

a mandrel, disposed within said hollow guide wire assembly, having a distal end terminating at said distal end of said guide wire assembly; and means for introducing light energy into a proximal end of said optical fiber bundle; and an exchange lead having a distal end connected to a proximal end of said hypo tube;

wherein said plug surrounds said optical fibers in said optical fiber bundle and said mandrel and bonds said optical fibers and said mandrel to said distal end of said hollow guide wire assembly; and wherein a proximal end of said mandrel terminates proximate to a proximal end of said exchange lead.

14. The fiber optic guide wire apparatus of claim 13 wherein said mandrel, said plug and said distal end of said optical fiber bundle are rotatable independent of a distal portion of said guide wire apparatus exclusive of said distal end.

15. The fiber optic guide wire apparatus of claim 13, wherein said outer jacket comprises a distal jacket and a wire coil.

16. The fiber optic guide wire apparatus of claim 13, wherein said mandrel comprises:

a base portion at said proximal end; and a flattened portion at said distal end.

17. The fiber optic guide wire apparatus of claim 16, wherein said mandrel further comprises an enlarged portion intermediate said base portion and said flattened portion.

18. The fiber optic guide wire apparatus of claim 17, wherein said enlarged portion is substantially coextensive with a proximal end of said outer jacket.

19. A fiber optic guide wire apparatus, comprising:

a hollow guide wire assembly comprising a hypo tube, and a hollow outer jacket, said hollow outer jacket having a proximal end connected to a distal end of said hypo tube, said hollow guide wire assembly having a distal end termination;

a plug disposed at a distal end of said hollow guide wire assembly and having a distal face flush with said distal end termination of said hollow guide wire assembly;

an optical fiber bundle disposed within said guide wire assembly and including a plurality of optical fibers, said optical fiber bundle having a distal face terminating at said distal face of said plug;

a mandrel, disposed within said hollow guide wire assembly, having a distal end terminating at said distal end of said guide wire assembly; and means for introducing light energy into a proximal end of said optical fiber bundle; and a torque knob disposed on said hypo tube, said mandrel being coupled to said hypo tube, said torque knob engaging said guide wire assembly to transmit torque applied to said knob through said mandrel to said distal end of said guide wire assembly;

wherein said plug surrounds said optical fibers in said optical fiber bundle and said mandrel and bonds said optical fibers and said mandrel to said distal end of said hollow guide wire assembly.

20. The fiber optic guide wire apparatus of claim 19, further comprising:

an exchange lead having a distal end connected to a proximal end of said hypo tube; and a tail tube having a distal end covering at least a proximal end of said exchange lead and a proximal end connected to said means for introducing light energy;

wherein said torque knob is disposed distal to a distal end of said tail tube and may be freely slid along said hypo tube and said exchange lead to remove said tail tube.

\* \* \* \* \*